US009409646B2

(12) United States Patent
Fleck

(10) Patent No.: US 9,409,646 B2
(45) Date of Patent: *Aug. 9, 2016

(54) METHODS AND SYSTEMS FOR PROVIDING AERIAL ASSISTANCE

(71) Applicant: Google Inc., Mountain View, CA (US)

(72) Inventor: Mathias Samuel Fleck, Milpitas, CA (US)

(73) Assignee: Google Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/854,012

(22) Filed: Sep. 14, 2015

(65) Prior Publication Data
US 2016/0001884 A1 Jan. 7, 2016

Related U.S. Application Data

(63) Continuation of application No. 14/076,236, filed on Nov. 10, 2013, now Pat. No. 9,158,304.

(51) Int. Cl.
*G05D 1/00* (2006.01)
*B64C 39/02* (2006.01)
*G05D 1/10* (2006.01)
(Continued)

(52) U.S. Cl.
CPC ............ *B64C 39/024* (2013.01); *G05D 1/0011* (2013.01); *G05D 1/101* (2013.01); *A61B 5/6887* (2013.01); *B64C 2201/128* (2013.01); *B64C 2201/141* (2013.01); *B64C 2201/146* (2013.01); *B64G 1/52* (2013.01); *G05D 1/00* (2013.01); *G05D 1/0027* (2013.01); *G05D 1/0044* (2013.01); *G05D 1/0094* (2013.01); *G05D 1/12* (2013.01); *G06K 2209/21* (2013.01); *G07C 5/008* (2013.01); *G08B 25/006* (2013.01)

(58) Field of Classification Search
CPC ........ G08B 25/006; G07C 5/008; B64G 1/52; B64C 39/024; B64C 2201/146; B64C 2201/141; B64C 2201/128; G05D 1/0011; G05D 1/0044; G05D 1/0094; G05D 1/0027; G05D 1/00; G05D 1/12; G05D 1/101; G06K 2209/21; A61B 5/6887
USPC ........ 701/2, 3, 23–25, 300; 455/404.1, 404.2, 455/412.1, 456.1, 567
See application file for complete search history.

(56) References Cited

U.S. PATENT DOCUMENTS 6,084,510 A * 7/2000 Lemelson ............ G08B 15/004 340/539.13
7,957,837 B2 6/2011 Ziegler et al.
(Continued)

Primary Examiner — Fadey Jabr
Assistant Examiner — Angelina Shudy
(74) Attorney, Agent, or Firm — McDonnell Boehnen Hulbert & Berghoff LLP

(57) ABSTRACT

Embodiments described herein may relate to systems and methods for navigating to an emergency situation. An alert device may be controlled to issue alerts to draw the attention of bystanders to associated supplies for a situation. An illustrative method involves (a) receiving, by a computing system, a transmission indicating a situation at a designated location; (b) the computing system determining an approximate target area associated with the designated location; (c) the computing system making a determination that an alert device is located within the approximate target area; and (d) in response to the determination that the alert device is located within the approximate target area, the computing system executing instructions to activate at least one alert on the alert device indicating the situation and the designated location of the situation.

10 Claims, 10 Drawing Sheets

(51) Int. Cl.

| | | |
|---|---|---|
| G05D 1/12 | (2006.01) | |
| G07C 5/00 | (2006.01) | |
| G08B 25/00 | (2006.01) | |
| B64G 1/52 | (2006.01) | |
| A61B 5/00 | (2006.01) | |

(56) References Cited

U.S. PATENT DOCUMENTS

| | | | |
|---|---|---|---|
| 8,020,482 B1 * | 9/2011 | McCants, Jr. | B64D 1/04 89/1.11 |
| 8,082,102 B2 * | 12/2011 | Ravenscroft | G01C 21/005 701/2 |
| 8,145,183 B2 | 3/2012 | Barbeau | |
| 8,155,671 B2 | 4/2012 | Wood et al. | |
| 8,271,584 B2 | 9/2012 | Vella et al. | |
| 8,489,060 B2 | 7/2013 | Sennett et al. | |
| 8,494,489 B2 | 7/2013 | Drennan | |
| 8,543,265 B2 | 9/2013 | Ekhaguere et al. | |
| 8,626,361 B2 | 1/2014 | Gerlock | |
| 8,639,396 B1 * | 1/2014 | Hirsch | G08G 5/0008 244/76 R |
| 8,818,705 B2 | 8/2014 | Spata | |
| 8,909,391 B1 | 12/2014 | Peeters et al. | |
| 8,930,044 B1 | 1/2015 | Peeters et al. | |
| 8,948,935 B1 | 2/2015 | Peeters et al. | |
| 8,983,682 B1 | 3/2015 | Peeters et al. | |
| 9,013,301 B2 * | 4/2015 | Williams | B62H 5/00 340/539.13 |
| 9,158,304 B2 * | 10/2015 | Fleck | |
| 9,253,453 B2 * | 2/2016 | Meidan | G08B 13/1965 |
| 9,262,929 B1 * | 2/2016 | Roy | G08G 5/0034 |
| 2002/0188522 A1 | 12/2002 | McCall et al. | |
| 2004/0056770 A1 * | 3/2004 | Metcalf | B64D 45/0015 340/574 |
| 2008/0144884 A1 * | 6/2008 | Habibi | 382/103 |
| 2008/0183344 A1 * | 7/2008 | Doyen | G08B 3/10 701/9 |
| 2010/0094485 A1 * | 4/2010 | Verlut | G01C 21/005 701/3 |
| 2010/0250022 A1 | 9/2010 | Hines et al. | |
| 2010/0269143 A1 | 10/2010 | Rabowsky | |
| 2011/0084162 A1 | 4/2011 | Goossen et al. | |
| 2011/0130636 A1 | 6/2011 | Daniel et al. | |
| 2011/0264311 A1 * | 10/2011 | Lee | H04N 7/183 701/15 |
| 2012/0226394 A1 | 9/2012 | Marcus | |
| 2012/0271491 A1 | 10/2012 | Spata | |
| 2013/0141540 A1 | 6/2013 | Persson et al. | |
| 2014/0018979 A1 | 1/2014 | Goossen et al. | |
| 2014/0025236 A1 | 1/2014 | Levien et al. | |
| 2014/0032034 A1 * | 1/2014 | Raptopoulos | G08G 5/0069 701/25 |
| 2014/0180914 A1 | 6/2014 | Abhyanker | |
| 2014/0192193 A1 | 7/2014 | Zufferey et al. | |
| 2014/0288730 A1 | 9/2014 | Fucke et al. | |
| 2015/0142211 A1 | 5/2015 | Shehata et al. | |
| 2015/0148988 A1 * | 5/2015 | Fleck | 701/2 |
| 2015/0183528 A1 * | 7/2015 | Walsh | B64F 1/32 701/3 |

* cited by examiner

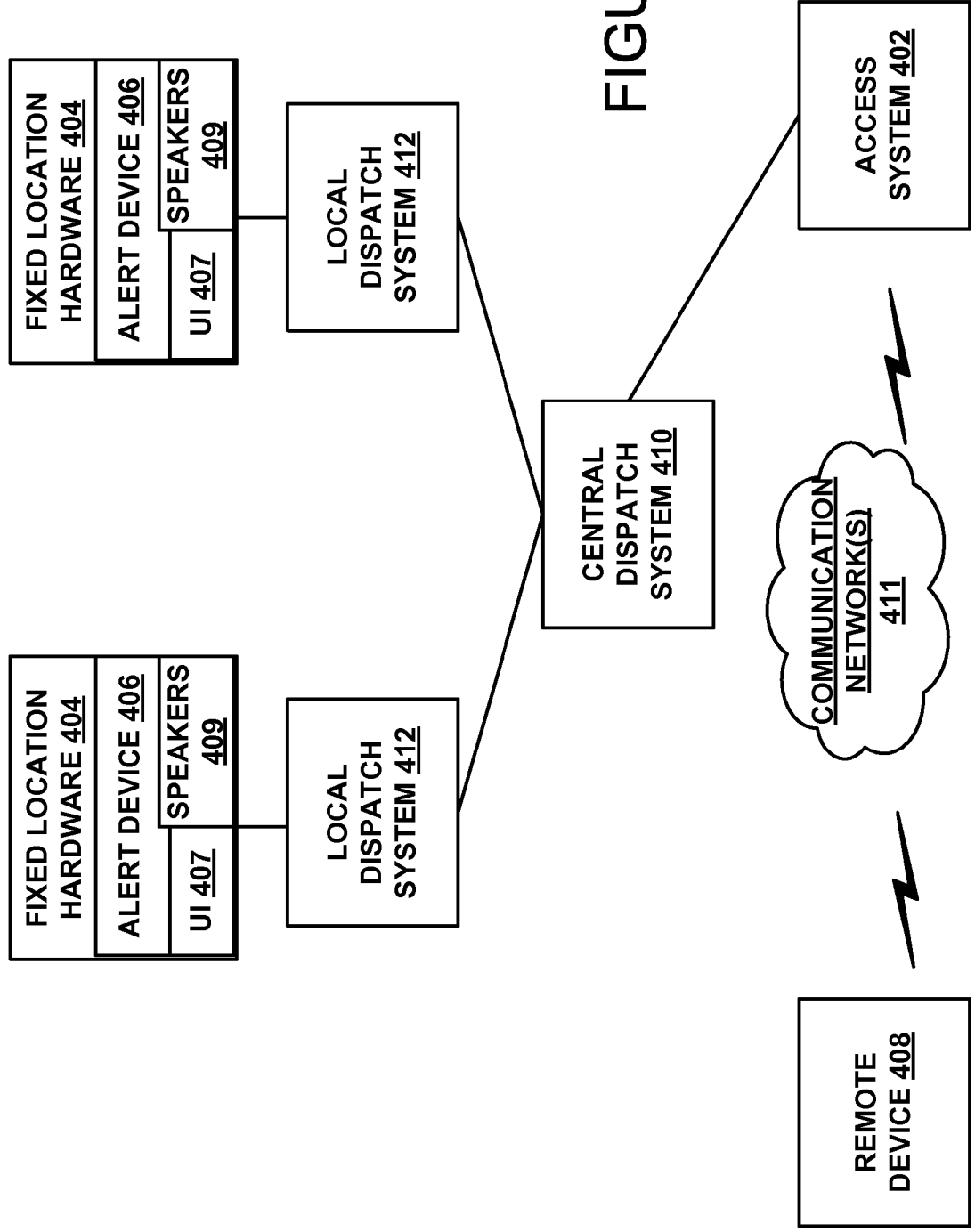

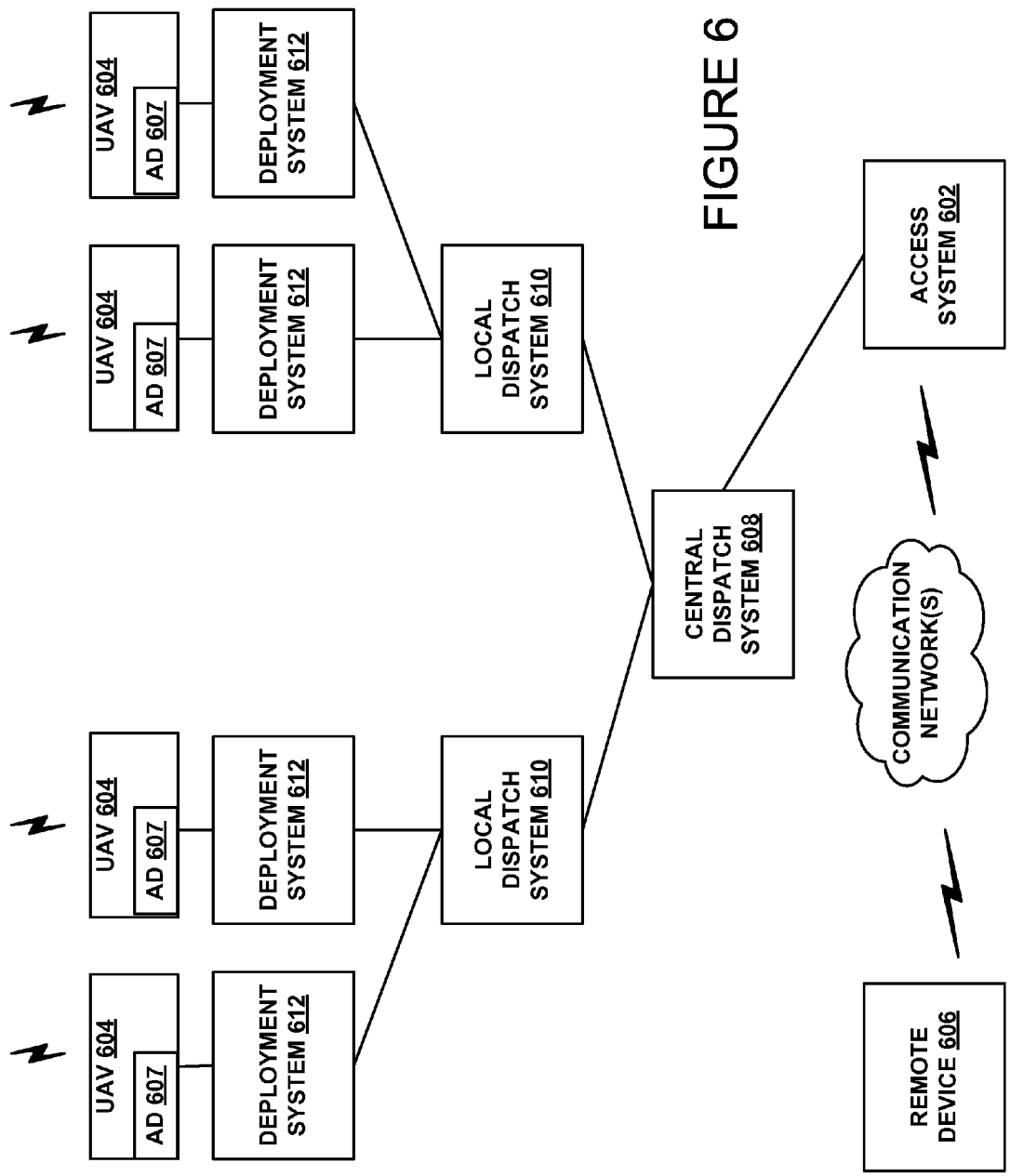

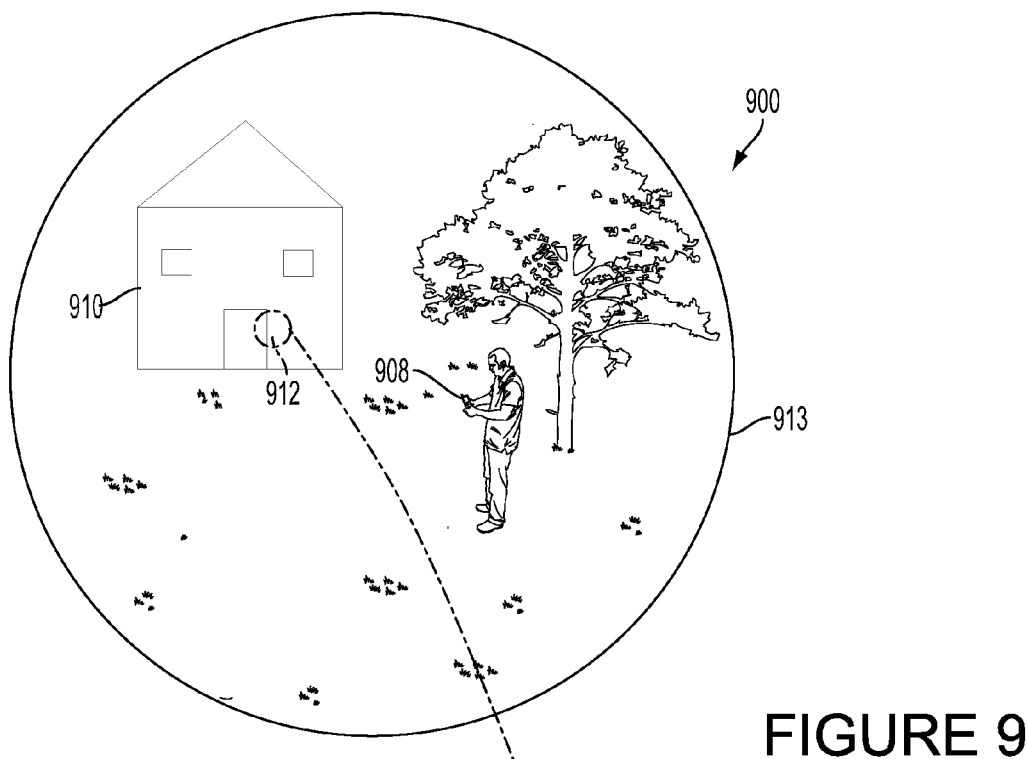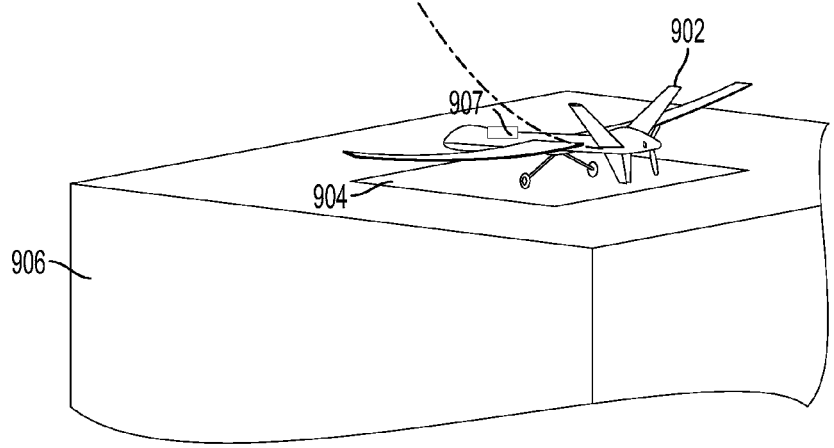
FIGURE 9

METHODS AND SYSTEMS FOR PROVIDING AERIAL ASSISTANCE

CROSS REFERENCE TO RELATED APPLICATIONS

The present application is a continuation of, and claims priority to, U.S. application Ser. No. 14/076,236, filed Nov. 10, 2013, which is hereby incorporated in its entirety herein by reference.

BACKGROUND

Unless otherwise indicated herein, the materials described in this section are not prior art to the claims in this application and are not admitted to be prior art by inclusion in this section.

Certain situations call for critical devices and/or deliveries to be transported to a scene of a situation where there is a need of aid. In such situations there is typically an urgency regarding the transportation of the devices and/or deliveries. Such devices and/or deliveries may comprise fixed-location hardware or may be located on an unmanned vehicle.

Fixed location hardware may include hardware or other items that are affixed to or kept at a particular location in or on a structure such as a building, sidewalk, street, vehicle, etc. The locations of such fixed-location hardware may be known and monitored by private or government entities, such as police, fire, school, or other institutions.

An unmanned vehicle, which may also be referred to as an autonomous vehicle, is a vehicle capable of travel without a physically-present human operator. An unmanned vehicle may operate in a remote-control mode, in an autonomous mode, or in a partially autonomous mode.

When an unmanned vehicle operates in a remote-control mode, a pilot or driver that is at a remote location can control the unmanned vehicle via commands that are sent to the unmanned vehicle via a wireless link. When the unmanned vehicle operates in autonomous mode, the unmanned vehicle typically moves based on pre-programmed navigation waypoints, dynamic automation systems, or a combination of these. Further, some unmanned vehicles can operate in both a remote-control mode and an autonomous mode, and in some instances may do so simultaneously.

Various types of unmanned vehicles exist for various different environments. For example, unmanned vehicles exist for operation in the air, on the ground, underwater, and in space. Unmanned vehicles also exist for hybrid operations in which multi-environment use is possible. Examples of hybrid unmanned vehicles include an amphibious craft that is capable of operation on land as well as on water or a floatplane that is capable of landing on water as well as on land.

SUMMARY

Methods and systems are provided for fixed-location hardware or unmanned aerial vehicles (UAVs) to provide support for a particular situation. Alert devices associated with the fixed-location hardware or the UAVs may be configured for communications with remote devices so that medical or other emergency or disaster relief support can communicate with and issue alerts through the alert devices. Accordingly, when either fixed-location hardware is within an approximate target area associated with a situation, or when a UAV reaches the predetermined approximate target location that is associated with a situation, the fixed-location hardware or the UAV may include an alert device that is activated to issue an alert to inform individuals near the alert device of the situation and provide instructions regarding what to do with the fixed-location hardware, the UAV, and/or any associated supplies. The methods and systems described herein allow for any individual within earshot or viewing capability of an alert device to move to the alert device, and determine (with help of instructions issued via the alert device) what to do with any associated supplies to come to the aid of those in need at the situation. The individuals do not need to have a subscription or other membership-type service to receive an alert, simply being in the vicinity of the alert allows an individual to participate in the transportation and operation of critical supplies.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 4 is a simplified block diagram illustrating a support system, according to an example embodiment.

FIG. 6 is a simplified block diagram illustrating a support system, according to an example embodiment.

FIG. 9 is an illustration of a scenario in which example methods could be implemented.

DETAILED DESCRIPTION

Figure 1:
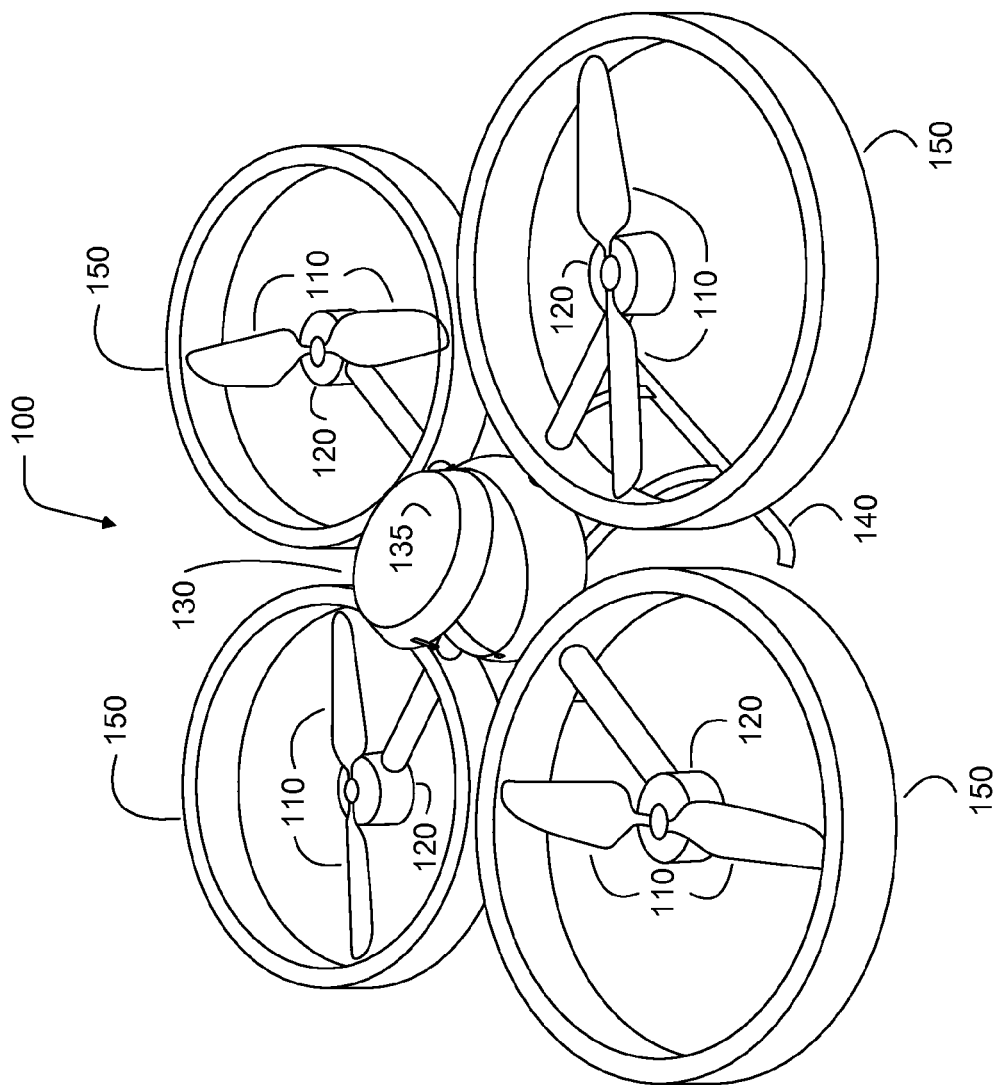
FIGS. 1, 2, 3A, and 3B are simplified illustrations of unmanned aerial vehicles, according to example embodiments.

Exemplary methods and systems are described herein. It should be understood that the word "exemplary" is used herein to mean "serving as an example, instance, or illustration." Any embodiment or feature described herein as "exemplary" or "illustrative" is not necessarily to be construed as preferred or advantageous over other embodiments or features. More generally, the embodiments described herein are not meant to be limiting. It will be readily understood that certain aspects of the disclosed systems and methods can be arranged and combined in a wide variety of different configurations, all of which are contemplated herein.

I. Overview

Embodiments described herein may relate to and/or may be implemented in a system in which fixed-location hardware or unmanned aerial vehicles (UAVs) are configured to provide support for a particular situation.

In an illustrative embodiment, a medical or other emergency or disaster relief support system ("support system") may include support hardware that is maintained at a particular location for medical, emergency, or disaster relief use ("fixed-location hardware"). Alert devices associated with the fixed-location hardware may be configured for communications with remote devices so that medical or other emergency or disaster relief support can communicate with and issue alerts through the alert devices.

In another illustrative embodiment, a medical or other emergency or disaster relief support system ("support system") may include a fleet of UAVs that are distributed throughout a geographic area, such as a city. The support system may be configured for communications with remote devices, such as mobile phones, so that medical or other emergency or disaster relief support can be requested by a person in need of such support (or by others on behalf of a person in need). The support system can then dispatch the appropriate UAV or UAVs to the scene of the situation in order to provide support. Alert devices associated with the UAVs may be remotely controlled or pre-activated to issue one or more alerts, notifying bystanders of the presence of the UAV and/or its associated contents.

In particular, a support system may include a fleet with a number of different types of UAVs, which are configured for different situations. As such, an illustrative support system may be configured to identify or classify the particular type of situation that is occurring, to select the appropriate UAV from those that are available, and to dispatch the selected UAV to the scene of the situation.

For some situations it may not be feasible to install fixed-location hardware at or navigate a UAV to the exact location of a medical situation. The fixed-location hardware may be determined to be located within an approximate target location but not exactly at the scene of the situation. In the case of a UAV, if GPS coordinates are reported, the reported GPS coordinates may, for various reasons, be somewhat inaccurate. In another example, the precise scene of the situation may be known but may not be immediately accessible by either the UAV or the fixed-location hardware, wherein the UAV or fixed-location hardware contents may need to be removed and transported by an individual to the scene of the situation.

To illustrate, consider a scenario where a person is having a heart attack in a stadium. In this scenario, GPS location information may only get a UAV so close to the person's actual location in the stadium; to the entrance of the stadium, for example. The UAV may not be able to enter the stadium and may have to land at the entrance of the stadium. Using the same scenario, fixed-location hardware may be present on a wall within the stadium and would need to be transported from the wall to the person's actual location in the stadium.

Accordingly, when either fixed-location hardware is within an approximate target area associated with a situation, or when a UAV reaches the predetermined approximate target location that is associated with a situation, the fixed-location hardware or the UAV may include an alert device that is activated to draw sensory attention to the fixed-location hardware or the UAV, wherein sensory attention comprises issuing one or more alerts to individuals within audio and/or visual proximity the alert device of the situation. The alert device may also provide instructions regarding what to do with the fixed-location hardware, the UAV, and/or any associated supplies. For example, such an alert device may comprise an automated audio (e.g., a loud noise, such as a repeated beep, honk, or a continuous siren) alert. In another example, the fixed-location hardware or the UAV may comprise an automated visual (e.g., a repeated light or a beacon of light emitted from the UAV) instead of or in addition to an audio alert. The audio alert may also comprise audio or visual instructions informing bystanders of a type of situation and urging the bystanders to pick up the fixed-location hardware, the UAV, or associated supplies, and take the desired items to the scene of the situation. The alert device may be operated remotely, or may be pre-programmed to activate one or more alerts at specified times or after the lapse of a time interval.

For instance, an alert may be pre-set to automatically and autonomously begin upon activation of a trigger. Such a trigger may be a UAV touching ground, for example. In another example, a trigger may comprise the UAV reaching a target location. Alternatively, or as a fallback process should the automatic alert not begin, the UAV might implement process that allows for full or partial control of the UAV by a remote operator, so that the remote operator can issue one or more of the alerts described above.

Such alert devices and associated methods and systems for navigating to an emergency situation are beneficial for a number of reasons, for example, to deliver critical supplies to the scene of a situation as efficiently as possible. The methods and systems described herein allow for any bystander within earshot or viewing capability of an alert device to move to the alert device, and determine (with help of instructions issued via the alert device) what to do with any associated supplies to come to the aid of those in need at the situation. The bystanders do not need to have a subscription or other membership-type service to receive an alert, simply being in the vicinity of the alert allows a bystander to participate in the transportation and operation of critical supplies. In this manner, even if medically-trained professionals or authorities such as police, firemen, and the like, are not nearby a scene of a situation, the delivery of urgently needed assistance by untrained bystanders who are near the scene of the situation can be accomplished. The methods and systems described herein may prevent the passage of critical seconds, minutes, or even hours before professionals or authorities may be able to arrive at the scene of the situation to deliver assistance.

It should be understood that the above embodiments, and other embodiments described herein, are provided for explanatory purposes, and are not intended to be limiting.

Furthermore, the term "situation" as used herein should be understood to include any situation to which government or private entity, such as a police department, a fire department, and/or an emergency medical services (EMS) entity, might dispatch its personnel. For example, an emergency situation to which a police car, fire truck, or ambulance might be dispatched may be considered a medical situation for purposes of this disclosure. Medical support may not be required at such emergency situations (e.g., when police are sent to the scene of a non-violent crime). Further, some non-emergency situations to which a police car, fire truck, ambulance, or the like might be dispatched may also be considered a situation for purposes of this disclosure. Thus, while exemplary embodiments may be described as being implemented to help provide emergency or medical support at the scene of a situation, those skilled in the art will understand that the fixed-location hardware, UAVs, and/or other aspects of the embodiments that are explicitly described herein can also apply in non-medical, non-emergency, and/or non-disaster relief applications.

II. Illustrative Unmanned Vehicles

The term "unmanned aerial vehicle," as used in this disclosure, refers to any autonomous or semi-autonomous vehicle that is capable of performing some functions without a physically-present human pilot. Examples of flight-related functions may include, but are not limited to, sensing its environment or operating in the air without a need for input from an operator, among others.

A UAV may be autonomous or semi-autonomous. For instance, some functions could be controlled by a remote human operator, while other functions are carried out autonomously. Further, a UAV may be configured to allow a remote operator to take over functions that can otherwise be controlled autonomously by the UAV. Yet further, a given type of function may be controlled remotely at one level of abstraction and performed autonomously at another level of abstraction. For example, a remote operator could control high level navigation decisions for a UAV, such as by specifying that the UAV should travel from one location to another (e.g., from the city hall in Palo Alto to the city hall in San Francisco), while the UAV's navigation system autonomously controls more fine-grained navigation decisions, such as the specific route to take between the two locations, specific flight controls to achieve the route and avoid obstacles while navigating the route, and so on. Other examples are also possible.

A UAV can be of various forms. For example, a UAV may take the form of a rotorcraft such as a helicopter or multicopter, a fixed-wing aircraft, a jet aircraft, a ducted fan aircraft, a lighter-than-air dirigible such as a blimp or steerable balloon, a tail-sitter aircraft, a glider aircraft, and/or an ornithopter, among other possibilities. Further, the terms "drone", "unmanned aerial vehicle system" ("UAVS"), or "unmanned aerial system" ("UAS") may also be used to refer to a UAV.

FIG. 1 is a simplified illustration of a UAV, according to an example embodiment. In particular, FIG. 1 shows an example of a rotorcraft 100 that is commonly referred to as a multicopter. Multicopter 100 may also be referred to as a quadcopter, as it includes four rotors 110. It should be understood that example embodiments may involve rotorcraft with more or less rotors than multicopter 100. For example, a helicopter typically has two rotors. Other examples with three or more rotors are possible as well. Herein, the term "multicopter" refers to any rotorcraft having more than two rotors, and the term "helicopter" refers to rotorcraft having two rotors.

Referring to multicopter 100 in greater detail, the four rotors 110 provide propulsion and maneuverability for the multicopter 100. More specifically, each rotor 110 includes blades that are attached to a motor 120. Configured as such the rotors may allow the multicopter 100 to take off and land vertically, to maneuver in any direction, and/or to hover. Furthermore, the pitch of the blades may be adjusted as a group and/or differentially, and may allow a multicopter 110 to perform three-dimensional aerial maneuvers such as an upside-down hover, a continuous tail-down "tic-toc," loops, loops with pirouettes, stall-turns with pirouette, knife-edge, immelmann, slapper, and traveling flips, among others. When the pitch of all blades is adjusted to perform such aerial maneuvering, this may be referred to as adjusting the "collective pitch" of the multicopter 100. Blade-pitch adjustment may be particularly useful for rotorcraft with substantial inertia in the rotors and/or drive train, but is not limited to such rotorcraft.

Additionally or alternatively, multicopter 100 may propel and maneuver itself adjust the rotation rate of the motors, collectively or differentially. This technique may be particularly useful for small electric rotorcraft with low inertia in the motors and/or rotor system, but is not limited to such rotorcraft.

Multicopter 100 also includes a central enclosure 130 with a hinged lid 135. The central enclosure may contain, e.g., control electronics such as an inertial measurement unit (IMU) and/or an electronic speed controller, batteries, other sensors, and/or a payload, among other possibilities.

The illustrative multicopter 100 also includes landing gear 140 to assist with controlled take-offs and landings. In other embodiments, multicopters and other types of UAVs without landing gear are also possible.

In a further aspect, multicopter 100 includes rotor protectors 150. Such rotor protectors 150 can serve multiple purposes, such as protecting the rotors 110 from damage if the multicopter 100 strays too close to an object, protecting the multicopter 100 structure from damage, and protecting nearby objects from being damaged by the rotors 110. It should be understood that in other embodiments, multicopters and other types of UAVs without rotor protectors are also possible. Further, rotor protectors of different shapes, sizes, and function are possible, without departing from the scope of the invention.

A multicopter 100 may control the direction and/or speed of its movement by controlling its pitch, roll, yaw, and/or altitude. To do so, multicopter 100 may increase or decrease the speeds at which the rotors 110 spin. For example, by maintaining a constant speed of three rotors 110 and decreasing the speed of a fourth rotor, the multicopter 100 can roll right, roll left, pitch forward, or pitch backward, depending upon which motor has its speed decreased. Specifically, the multicopter may roll in the direction of the motor with the decreased speed. As another example, increasing or decreasing the speed of all rotors 110 simultaneously can result in the multicopter 100 increasing or decreasing its altitude, respectively. As yet another example, increasing or decreasing the speed of rotors 110 that are turning in the same direction can result in the multicopter 100 performing a yaw-left or yaw-right movement. These are but a few examples of the different types of movement that can be accomplished by independently or collectively adjusting the RPM and/or the direction that rotors 110 are spinning.

Figure 2:
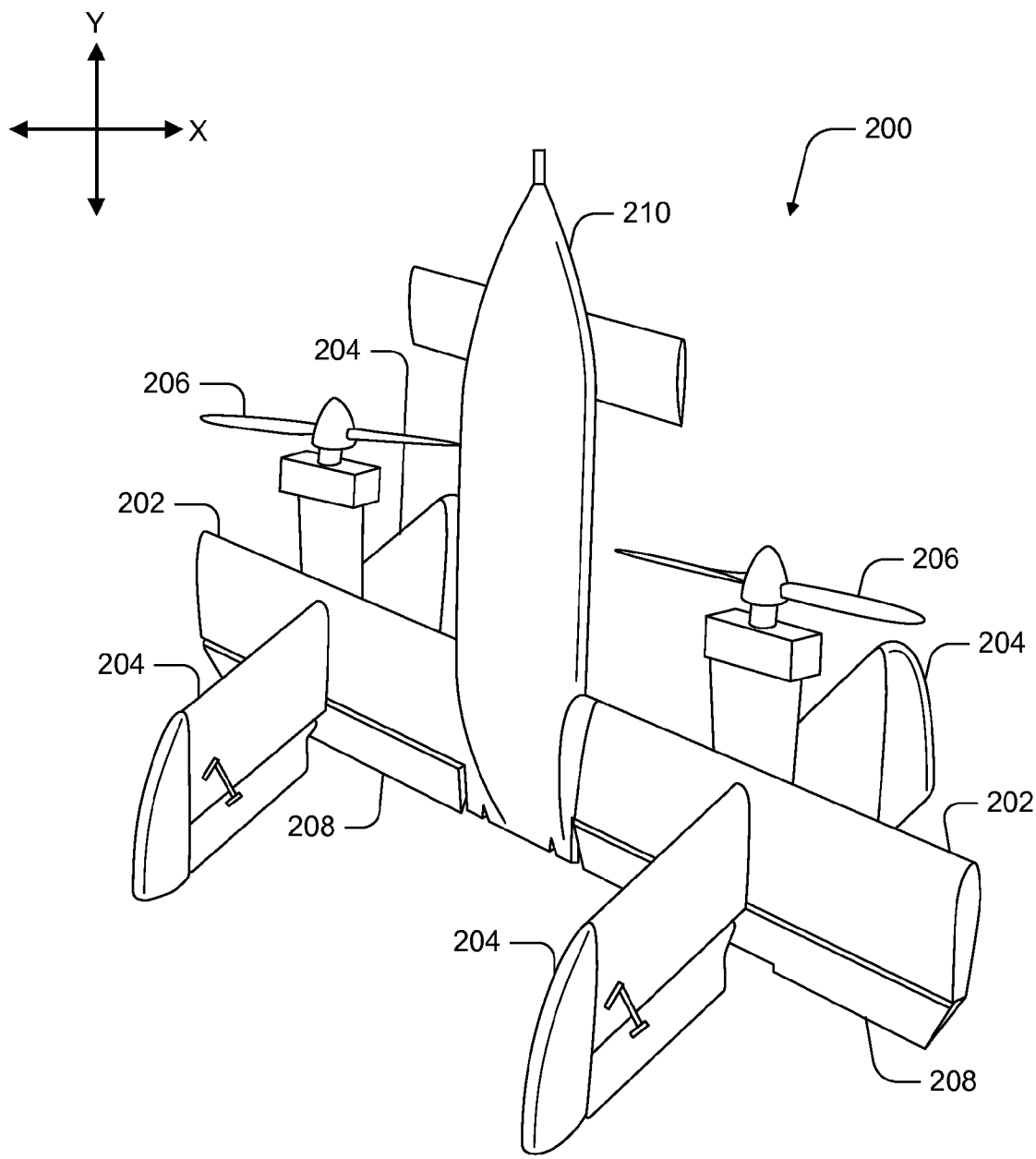

FIG. 2 is a simplified illustration of a UAV, according to an example embodiment. In particular, FIG. 2 shows an example of a tail-sitter UAV 200. In the illustrated example, the tail-sitter UAV 200 has fixed wings 202 to provide lift and allow the UAV to glide horizontally (e.g., along the x-axis, in a position that is approximately perpendicular to the position shown in FIG. 2). However, the fixed wings 202 also allow the tail-sitter UAV 200 take off and land vertically on its own.

For example, at a launch site, tail-sitter UAV 200 may be positioned vertically (as shown) with fins 204 and/or wings 202 resting on the ground and stabilizing the UAV in the vertical position. The tail-sitter UAV 200 may then take off by operating propellers 206 to generate the upward thrust (e.g., a thrust that is generally along the y-axis). Once at a suitable altitude, the tail-sitter UAV 200 may use its flaps 208 to reorient itself in a horizontal position, such that the fuselage 210 is closer to being aligned with the x-axis than the y-axis. Positioned horizontally, the propellers 206 may provide forward thrust so that the tail-sitter UAV 200 can fly in a similar manner as a typical airplane.

Variations on the illustrated tail-sitter UAV 200 are possible. For instance, tail-sitters UAVs with more or less propellers, or that utilize a ducted fan or multiple ducted fans, are also possible. Further, different wing configurations with more wings (e.g., an "x-wing" configuration with four wings), with less wings, or even with no wings, are also possible. More generally, it should be understood that other types of tail-sitter UAVs and variations on the illustrated tail-sitter UAV 200 are also possible.

As noted above, some embodiments may involve other types of UAVs, in addition or in the alternative to multicopters. For instance, FIGS. 3A and 3B are simplified illustrations of other types of UAVs, according to example embodiments.

Figure 3A:
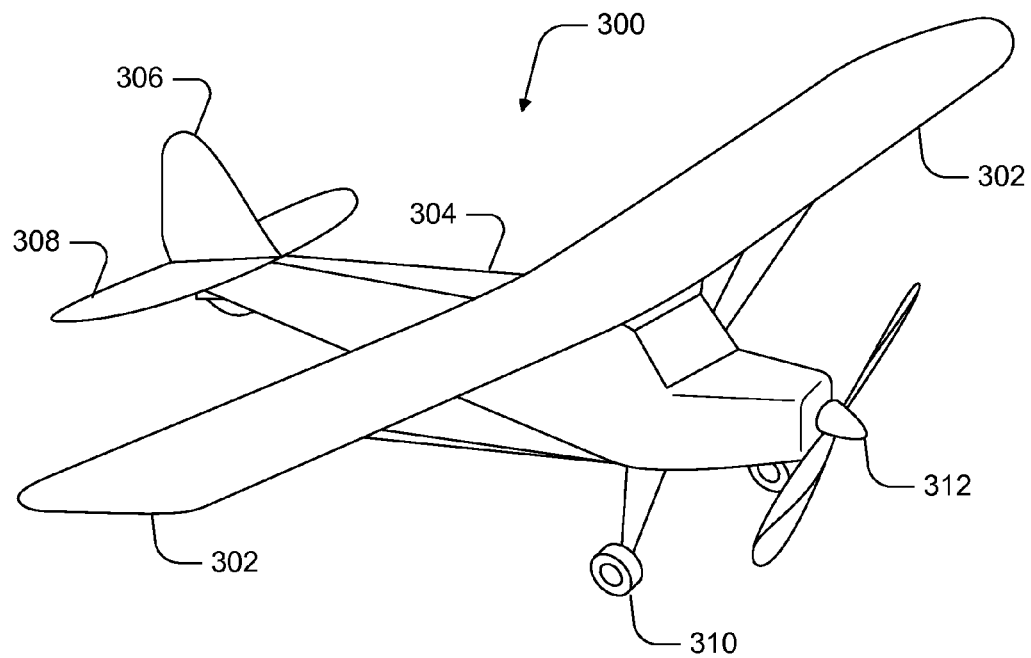

In particular, FIG. 3A shows an example of a fixed-wing aircraft 300, which may also be referred to as an airplane, an aeroplane, or simply a plane. A fixed-wing aircraft 300, as the name implies, has stationary wings 302 that generate lift based on the wing shape and the vehicle's forward airspeed. This wing configuration is different from a rotorcraft's configuration, which produces lift through rotating rotors about a fixed mast, and an ornithopter's configuration, which produces lift by flapping wings.

FIG. 3A depicts some common structures used in a fixed-wing aircraft 300. In particular, fixed-wing aircraft 300 includes a fuselage 304, two horizontal wings 302 with an airfoil-shaped cross section to produce an aerodynamic force, a vertical stabilizer 306 (or fin) to stabilize the plane's yaw (turn left or right), a horizontal stabilizer 308 (also referred to as an elevator or tailplane) to stabilize pitch (tilt up or down), landing gear 310, and a propulsion unit 312, which can include a motor, shaft, and propeller.

Figure 3B:
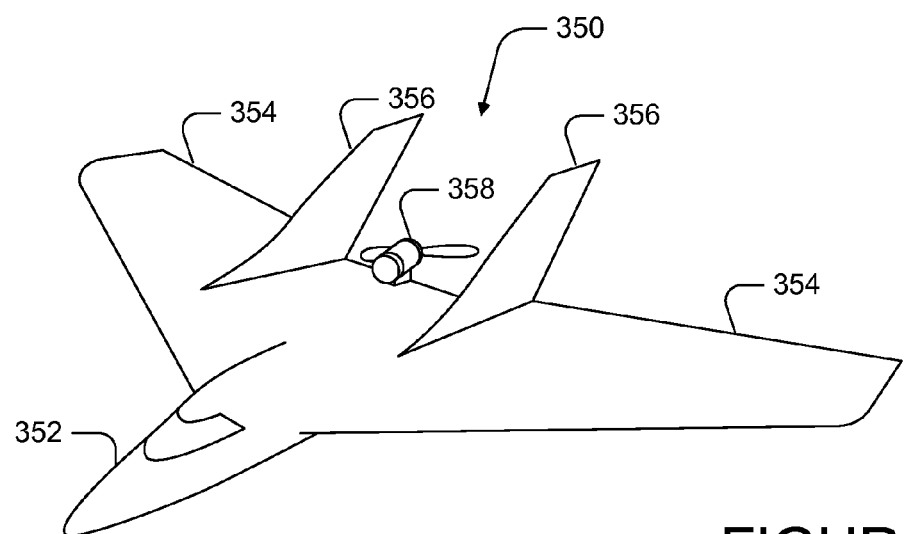

FIG. 3B shows an example of an aircraft 350 with a propeller in a pusher configuration. The term "pusher" refers to the fact that the propulsion unit 358 is mounted at the back of the aircraft and "pushes" the vehicle forward, in contrast to the propulsion unit being mounted at the front of the aircraft. Similar to the description provided for FIG. 3A, FIG. 3B depicts common structures used in the pusher plane: a fuselage 352, two horizontal wings 354, vertical stabilizers 356, and a propulsion unit 358, which can include a motor, shaft, and propeller.

UAVs can be launched in various ways, using various types of launch systems (which may also be referred to as deployment systems). A very simple way to launch a UAV is a hand launch. To perform a hand launch, a user holds a portion of the aircraft, preferably away from the spinning rotors, and throws the aircraft into the air while contemporaneously throttling the propulsion unit to generate lift.

Rather than using a hand launch procedure in which the person launching the vehicle is exposed to risk from the quickly spinning propellers, a stationary or mobile launch station can be utilized. For instance, a launch system can include supports, angled and inclined rails, and a backstop. The aircraft begins the launch system stationary on the angled and inclined rails and launches by sufficiently increasing the speed of the propeller to generate forward airspeed along the incline of the launch system. By the end of the angled and inclined rails, the aircraft can have sufficient airspeed to generate lift. As another example, a launch system may include a rail gun or cannon, either of which may launch a UAV by thrusting the UAV into flight. A launch system of this type may launch a UAV quickly and/or may launch a UAV far towards the UAV's destination. Other types of launch systems may also be utilized.

In some cases, there may be no separate launch system for a UAV, as a UAV may be configured to launch itself. For example, a "tail sitter" UAV typically has fixed wings to provide lift and allow the UAV to glide, but also is configured to take off and land vertically on its own. Other examples of self-launching UAVs are also possible.

In a further aspect, various other types of unmanned vehicles may be utilized to provide remote emergency, disaster, or medical support. Such vehicles may include, for example, unmanned ground vehicles (UGVs), unmanned space vehicles (USVs), and/or unmanned underwater vehicles (UUVs). A UGV may be a vehicle which is capable of sensing its own environment and navigating surface-based terrain without input from a driver. Examples of UGVs include watercraft, cars, trucks, buggies, motorcycles, treaded vehicles, and retrieval duck decoys, among others. A UUV is a vehicle that is capable of sensing its own environment and navigating underwater on its own, such as a submersible vehicle. Other types of unmanned vehicles are possible as well.

III. Illustrative Fixed-Location Hardware

The term "fixed-location hardware," as used in this disclosure, refers to any device or assembly that is maintained at a particular location for medical, emergency, or disaster relief use. Fixed location hardware may be configured to be physically accessed and transported by individuals, machines, and the like for use in providing aid for a situation. Unlike a UAV as described herein, fixed-location hardware is generally not configured to move from one location to another via remote control.

Examples of fixed-location hardware may include, but are not limited to, fire hydrants, fire extinguishers, automatic external defibrillators (AED), and emergency supplies, such as containers of water, food, and first aid kits, among others.

Fixed location hardware may be networked to one or more alert devices, to other fixed-location hardware, and/or to a government or private entity, such as a police department, a fire department, and/or an emergency medical services (EMS) entity, for example.

IV. Illustrative Support Systems

As noted above, fixed-location hardware and/or UAVs may be used to provide remote medical, emergency, disaster relief, or other such support.

FIG. 4 is a simplified block diagram illustrating a support system, according to an example embodiment.

In an illustrative support system 400, an access system 402 may allow for interaction with a network of support fixed-location hardware 404. In some embodiments, an access system 402 may be a computing system that allows for human-controlled activation of an alert device 406 attached to the fixed-location hardware 404.

As a specific example, access system 402 could be a computing system at a police station or a fire station. Accordingly, a human operator at the police or fire station may receive an indication that a situation exists from a remote device 408 (e.g., a phone call, text message, etc.). The operator may then determine that medical and/or emergency support is appropriate and utilize access system 402 to activate the alert device 406 in an effort to draw attention to the alert device 406 and associated fixed-location hardware 404. For instance, an operator, upon a determination that medical and/or emergency support is appropriate, may utilize access system 402 to activate the alert device 406 affixed to or in communication with the fixed-location hardware 404 to alert any person or persons within earshot of the alert device ("bystanders") of a situation and instruct the bystanders to take and/or operate one or more components of the fixed-location hardware.

The alert device 406 may be configured with one or more speakers 409 to issue an audio (e.g., a loud noise, such as a repeated beep, honk, or a continuous siren) alert. Such audio alerts are generally configured to comprise a volume sufficient to attract the attention of a person who is in the vicinity of the alert device 406. In another example, alert device 406 may be configured to issue a visual (e.g., a repeated, flashing, or blinking light, or a beacon emitted from the alert device) alert instead of or in addition to an audio alert. The visual alert is designed to attract the attention of a person who is in the vicinity of the alert device 406. Both audio and visual alerts may be used simultaneously, or in an alternating pattern, for example. The alerts may expire at the end of a pre-determined time interval, upon the occurrence of a trigger event, and/or upon remote control by an operator of the access system 402. An example trigger event may be a detected change in location of the alert device, such as when a person picks up and transports the alert device to a scene of a situation.

The alert device 406 may include or otherwise provide a user interface (UI) 407 via which one or more persons can view information, such as instructions informing of a type or nature of a situation and urging any bystanders to pick up the fixed-location hardware 404 and/or any associated support items and transport the support items to a desired location, such as a scene of a situation. The instructions may also include information regarding how to operate support items to provide support at the scene of a situation. A user may thus be able to interact with the alert device 406 via the UI 407.

Instructions such as those described above may instead and/or in addition be delivered to bystanders in an audio manner, over the one or more speakers 409 on the alert device 406.

In an illustrative arrangement, central dispatch system 410 may be a server or group of servers, which is configured to receive dispatch messages requests and/or dispatch instructions from access system 402. A central dispatch system 410 may be further configured to route such requests or instructions to local dispatch systems 412. To provide such functionality, central dispatch system 410 may communicate with access system 402 via a data network, such as the Internet or a private network that is established for communications between access systems and automated dispatch systems.

In some embodiments, when central dispatch system 410 receives a request for medical support from an access system 402, central dispatch system 410 may select a specific alert device 406 associated with a fixed-location hardware 404 to activate. The central dispatch system 410 may accordingly instruct the local dispatch system 412 that is associated with the selected alert device 406 to activate the selected alert device 406, or to send instructions to the alert device 406 to activate the alert device 406.

As a specific example, central dispatch system 410 may receive a request for emergency support that indicates a certain type of situation and a location where the situation is occurring. Take, for instance, a request for support in a building that has caught fire. In this scenario, the central dispatch system 410 may evaluate the locations of various alert devices 406 associated with the appropriate fixed-location hardware (e.g., fire extinguishers or fire hydrants) to select the closest available alert device 406 to the building with the fire.

In an example configuration, a local dispatch system 412 may be implemented in a computing system at the same location as the alert devices 406 that it controls. In other embodiments, a local dispatch system 412 could be implemented at a location that is remote from its associated alert devices 406.

Numerous variations on and alternatives to the illustrated configuration of medical support system 400 are possible. For example, in some embodiments, a user of a remote device 408 could request medical support directly from a central dispatch system 410. To do so, an application may be implemented on a remote device 408 that allows the user to provide information regarding a medical situation, and generate and send a data message to request medical support. In such an embodiment, central dispatch system 410 may include automated functionality to handle requests that are generated by such an application, evaluate such requests, and, if appropriate, coordinate with an appropriate local dispatch system 412 to activate an alert device 406.

The remote device 408 may take various forms. Generally, remote device 408 may be any device via which a request for medical support can be made and/or via which a situation that may require or benefit from medical support can be reported. For instance, remote device 408 may be a mobile phone, tablet computer, laptop computer, personal computer, or any network-connected computing device. Further, in some instances, remote device 408 may not be a computing device.

As an example, a standard telephone, which allows for communication via plain old telephone service (POTS), may serve as a remote device 408.

Further, remote device 408 may be configured to communicate with access system 402 via one or more types of communication network(s) 411. For example, a remote device 408 could communicate with access system 402 (or via a human operator of the access system) by placing a phone call over a POTS network, a cellular network, and/or a data network such as the Internet. Other types of networks may also be utilized.

Further, in some implementations, some or all of the functionality that is attributed herein to central dispatch system 410, local dispatch system(s) 412, and/or access system 402, could be combined in a single system, implemented in a more complex system, and/or redistributed among central dispatch system 410, local dispatch system(s) 412, and/or access system 402 in various ways.

Yet further, while each local dispatch system 412 is shown as having one associated device 406 and fixed-location hardware 404, a given local dispatch system 412 may have more associated devices 406 and fixed-location hardware 404. Similarly, while central dispatch system 410 is shown as being in communication with two local dispatch systems 412, a central dispatch system may be in communication with more or less local dispatch systems 412.

Figure 5A:
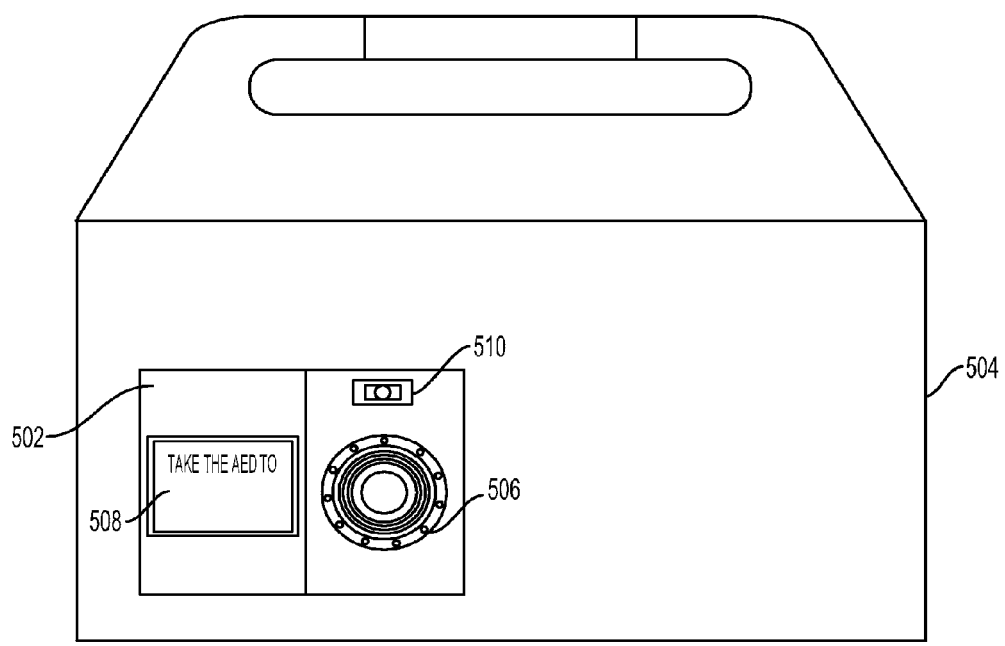
FIGS. 5A and 5B are illustrations of example alert devices on fixed-location hardware.

FIG. 5a is an illustration of an example implementation of an alert device 502 on an automatic external defibrillator (AED) 504. The alert device 502 comprises a wireless radio with a speaker 506, a display 508, and a visual alert system 510. The display 508 may comprise a computerized LED or LCD display, and may be configured to display instructions to a user (as shown), and/or to provide for user interaction via a keyboard or the like. The alert device may also comprise a power source (not shown). The power source may comprise a battery, for example. Other sources of power may also be contemplated. The speaker 506 may issue audio alerts such as those described herein. The visual alert system 510 may issue a bright light or other visual alert, such as those described herein.

The alert device 502 may be removably attachable to AED 504, such as with screws, bolts, an adhesive, Velcro®, or a number of other attachment mechanisms. In other embodiments, the alert device 502 may be integral with AED 504 or a packaging of AED 504. The alert device 502 may be networked to a system such as system 400, and may be remotely controlled via such a system to activate one or more audio and/or visual alerts.

Figure 5B:
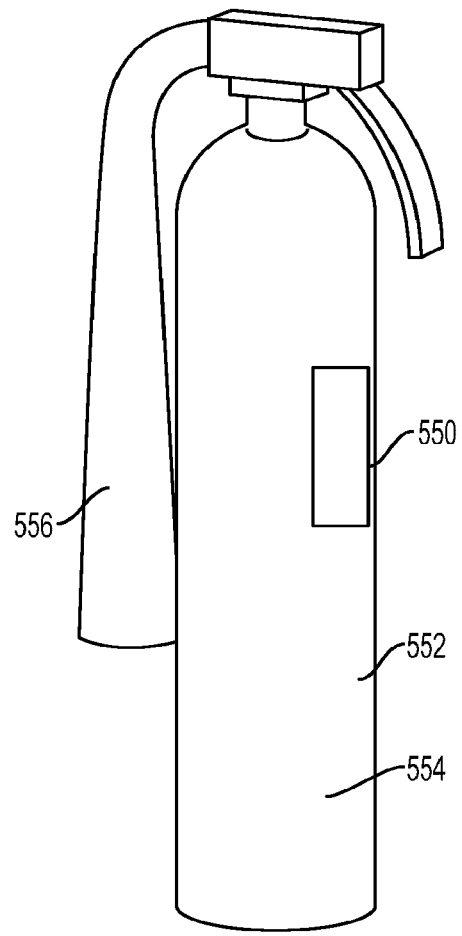

FIG. 5b is an illustration of an example implementation of an alert device 550 on a fire extinguisher 552. The alert device 550 may be the same as or similar to the alert device 502 described with reference to FIG. 5A, may be networked to a system such as system 400, and may be remotely controlled to activate one or more alerts. Although the alert device 550 is shown in FIG. 5B to be attached to the gas tank portion 554 of the fire extinguisher 552, the alert device 550 may be present on other portions of the fire extinguisher 552, such as the handle 556, for example. In instances where the fire extinguisher 552 is maintained within a casing, the alert device 552 may be attached or otherwise affixed to the casing instead of the extinguisher itself.

FIG. 6 is a simplified block diagram illustrating a support system 600, according to an example embodiment.

In an illustrative support system 600, an access system 602 may allow for interaction with, control of, and/or utilization of a network of support UAVs 604. In some embodiments, an access system 602 may be a computing system that allows for human-controlled dispatch of UAVs 604. The UAVs 604 each include an alert device (AD) 607. Each AD 607 may include a user interface (UI) and one or more speakers (not shown in FIG. 6), as shown and described to issue alerts and instructions such as for the alert device 407 of FIG. 4. The ADs 607 may be configured for remote communication and/or control by the access system 602.

As a specific example, access system 602 could be a computing system at a police station or a fire station. Accordingly, a human operator at the police or fire station may receive an indication that a situation exists from a remote device 606 (e.g., a phone call, text message, etc.). The operator may then determine that medical and/or emergency support is appropriate and utilize access system 602 to dispatch one or more UAVs to provide the appropriate medical support.

Access system 602 may provide for remote operation of a UAV 604 and associated AD 607. For instance, an access system 602 may allow an operator to control the flight of a UAV 604 and may allow an operator to control the activation and operation of one or more alerts of an AD 607. As a specific example, an operator may use an access system to dispatch a UAV 604 to the scene of a medical situation. The UAV 604 may then autonomously navigate to the general area where the medical situation is believed to exist (e.g., a stadium). At this point, the operator may use the access system 602 to take over control of the UAV 604, and navigate the UAV closer to the particular person in need of medical support. The operator may then activate one or more alerts through the AD 607 to draw the attention of any bystanders to pick up and transport the UAV and/or associated supplies to the precise scene of the situation (e.g., to the person's seat within the stadium). Other examples are also possible.

In an illustrative embodiment, UAVs 604 may take various forms. For example, each UAV 604 may be a UAV such as those illustrated in FIGS. 1, 2, 3A, and 3B. However, medical support system 600 may also utilize other types of UAVs without departing from the scope of the invention. In some implementations, all UAVs 604 may be of the same or a similar configuration. However, in other implementations, UAVs 604 may include a number of different types of UAVs. For instance, UAVs 604 may include a number of types of UAVs, with each type of UAV being configured for a different type or types of medical support.

A remote device 606 may take various forms. Generally, a remote device 606 may be any device via which a request for medical support can be made and/or via which a situation that may require or benefit from medical support can be reported. For instance, a remote device 606 may be a mobile phone, tablet computer, laptop computer, personal computer, or any network-connected computing device. Further, in some instances, remote device 606 may not be a computing device. As an example, a standard telephone, which allows for communication via plain old telephone service (POTS), may serve as a remote device 606.

Further, a remote device 606 may be configured to communicate with access system 602 via one or more types of communication network(s) 614. For example, a remote device 606 could communicate with access system 602 (or via a human operator of the access system) by placing a phone call over a POTS network, a cellular network, and/or a data network such as the Internet. Other types of networks may also be utilized.

As noted above, a remote device 606 may be configured to allow a user to request medical support. For example, a person may use their mobile phone, a POTS phone, or a VoIP phone, to place an emergency call (e.g., a 9-1-1 call) and request that medical support be provided at the scene of an accident.

Further, note that a request for medical support need not be explicit. For instance, a person may place a 9-1-1 call to report an emergency situation. When the 9-1-1 operator receives such a call, the operator may evaluate the information that is provided and decide that medical support is appropriate. Accordingly, the operator may use an access system 602 to dispatch a UAV 604.

In a further aspect, a remote device 606 may be configured to determine and/or provide an indication of its own location. For example, remote device 606 may include a GPS system so that it can include GPS location information (e.g., GPS coordinates) in a communication to an access system 602 and/or to a dispatch system such as central dispatch system 608. As another example, a remote device 606 may use a technique that involves triangulation (e.g., between base stations in a cellular network) to determine its location. Alternatively, another system such as a cellular network may use a technique that involves triangulation to determine the location of a remote device 606, and then send a location message to the remote device 606 to inform the remote device of its location. Other location-determination techniques are also possible.

In an illustrative arrangement, central dispatch system 608 may be a server or group of servers, which is configured to receive dispatch messages requests and/or dispatch instructions from an access system 602. Such dispatch messages may request or instruct the central dispatch system 608 to coordinate the deployment of UAVs for remote medical support. A central dispatch system 608 may be further configured to route such requests or instructions to local dispatch systems 610. To provide such functionality, central dispatch system 608 may communicate with access system 602 via a data network, such as the Internet or a private network that is established for communications between access systems and automated dispatch systems.

In the illustrated configuration, central dispatch system 608 may be configured to coordinate the dispatch of UAVs 604 from a number of different local dispatch systems 610. As such, central dispatch system 608 may keep track of which UAVs 604 are located at which local dispatch systems 610, which UAVs 604 are currently available for deployment, and/or which medical situation or situations each of the UAVs 604 is configured for. Additionally or alternatively, each local dispatch system 610 may be configured to track which of its associated UAVs 604 are currently available for deployment and/or which medical situation or situations each of its associated UAVs is configured for.

In some embodiments, when central dispatch system 608 receives a request for medical support from an access system 602, central dispatch system 608 may select a specific UAV 604 to dispatch. The central dispatch system 608 may accordingly instruct the local dispatch system 610 that is associated with the selected UAV to dispatch the selected UAV. The local dispatch system 610 may then operate its associated deployment system 612 to launch the selected UAV.

As a specific example, central dispatch system 608 may receive a request for medical support that indicates a certain type of medical situation and a location where the situation is occurring. Take, for instance, a request for medical support at the home of a person who appears to have suffered from cardiac arrest. In this scenario, the central dispatch system 608 may evaluate the fleet of UAVs 604 to select the closest available UAV to the person's home that is configured to provide medical support when a heart attack has occurred. Alternatively, the central dispatch system 608 may select an available UAV that is within a certain distance from the person's home (which may or may not be the closest), and which is configured to provide medical support when cardiac arrest has occurred.

In other embodiments, a central dispatch system 608 may forward a request for medical support to a local dispatch system 610 that is near the location where the support is requested, and leave the selection of a particular UAV 604 to the local dispatch system 610. For instance, in a variation on the above example, central dispatch system 608 may forward a request for medical support at the home of a person who appears to have suffered from a heart attack to the local dispatch system 610 that is closest to, or within a certain distance from, the person's home. Upon receipt of the request, the local dispatch system 610 may then determine which of its associated UAVs is configured to provide medical support to a heart-attack victim, and deploy this UAV.

In an example configuration, a local dispatch system 610 may be implemented in a computing system at the same location as the deployment system or systems 612 that it controls. For example, in some embodiments, a local dispatch system 610 could be implemented by a computing system at a building, such as a fire station, where the deployment systems 612 and UAVs 604 that are associated with the particular local dispatch system 610 are also located. In other embodiments, a local dispatch system 610 could be implemented at a location that is remote to its associated deployment systems 612 and UAVs 604.

Upon arriving at a target location, an AD 607 on UAV 604 may be activated by an operator via access system 602 to issue one or more alerts (such as audio and visual alerts described with reference to FIG. 4). Alternatively, AD 607 may have one or more alarms that are pre-set to activate upon the occurrence of a trigger event, such as UAV 604 touching ground, for example. Other trigger events, such as UAV 604 reaching a predetermined area or location, may also be used. The alerts may expire at the end of a pre-determined time interval, upon the occurrence of a trigger event, and/or upon remote control by an operator of the access system 602. An example trigger event may be a detected change in location of the alert device, such as when a person picks up and transports the alert device to a scene of a situation.

Numerous variations on and alternatives to the illustrated configuration of medical support system 600 are possible. For example, in some embodiments, a user of a remote device 606 could request medical support directly from a central dispatch system 608. To do so, an application may be implemented on a remote device 606 that allows the user to provide information regarding a medical situation, and generate and send a data message to request medical support. Such an application might also allow the user to request a particular type of medical support (e.g., by requesting that a UAV deliver a certain kind of medicine). In such an embodiment, central dispatch system 608 may include automated functionality to handle requests that are generated by such an application, evaluate such requests, and, if appropriate, coordinate with an appropriate local dispatch system 610 to deploy a UAV.

Further, in some implementations, some or all of the functionality that is attributed herein to central dispatch system 608, local dispatch system(s) 610, access system 602, and/or deployment system(s) 612 could be combined in a single system, implemented in a more complex system, and/or redistributed among central dispatch system 608, local dispatch system(s) 610, access system 602, and/or deployment system(s) 612 in various ways.

Yet further, while each local dispatch system 610 is shown as having two associated deployment systems, a given local dispatch system 610 may have more or less associated deployment systems. Similarly, while central dispatch system 608 is shown as being in communication with two local dispatch systems 610, a central dispatch system may be in communication with more or less local dispatch systems 610.

In a further aspect, a deployment system 612 may take various forms. In general, a deployment system may take the form of or include a system for physically launching a UAV 604. Further, a deployment system 612 may be configured to launch one particular UAV 604, or to launch multiple UAVs 604. A deployment system 612 may further be configured to provide additional functions, including for example, diagnostic-related functions such as verifying system functionality of the UAV, verifying functionality of devices that are housed within a UAV (e.g., such as a defibrillator, a mobile phone, or an HMD), and/or maintaining devices or other items that are housed in the UAV (e.g., by charging a defibrillator, mobile phone, or HMD, or by checking that medicine has not expired).

In some embodiments, the deployment systems 612 and their corresponding UAVs 604 (and possibly associated local dispatch systems 610) may be strategically distributed throughout an area such as a city. For example, deployment systems 612 may be located on the roofs of certain municipal buildings, such as fire stations, which can thus serve as the dispatch locations for UAVs 604. Fire stations may function well for UAV dispatch, as fire stations tend to be distributed well with respect to population density, their roofs tend to be flat, and the use of firehouse roofs as leased spaces for UAV dispatch could further the public good. However, deployment systems 612 (and possibly the local dispatch systems 610) may be distributed in other ways, depending upon the particular implementation.

IV. Illustrative Components of a Medical-Support UAV

Figure 7:
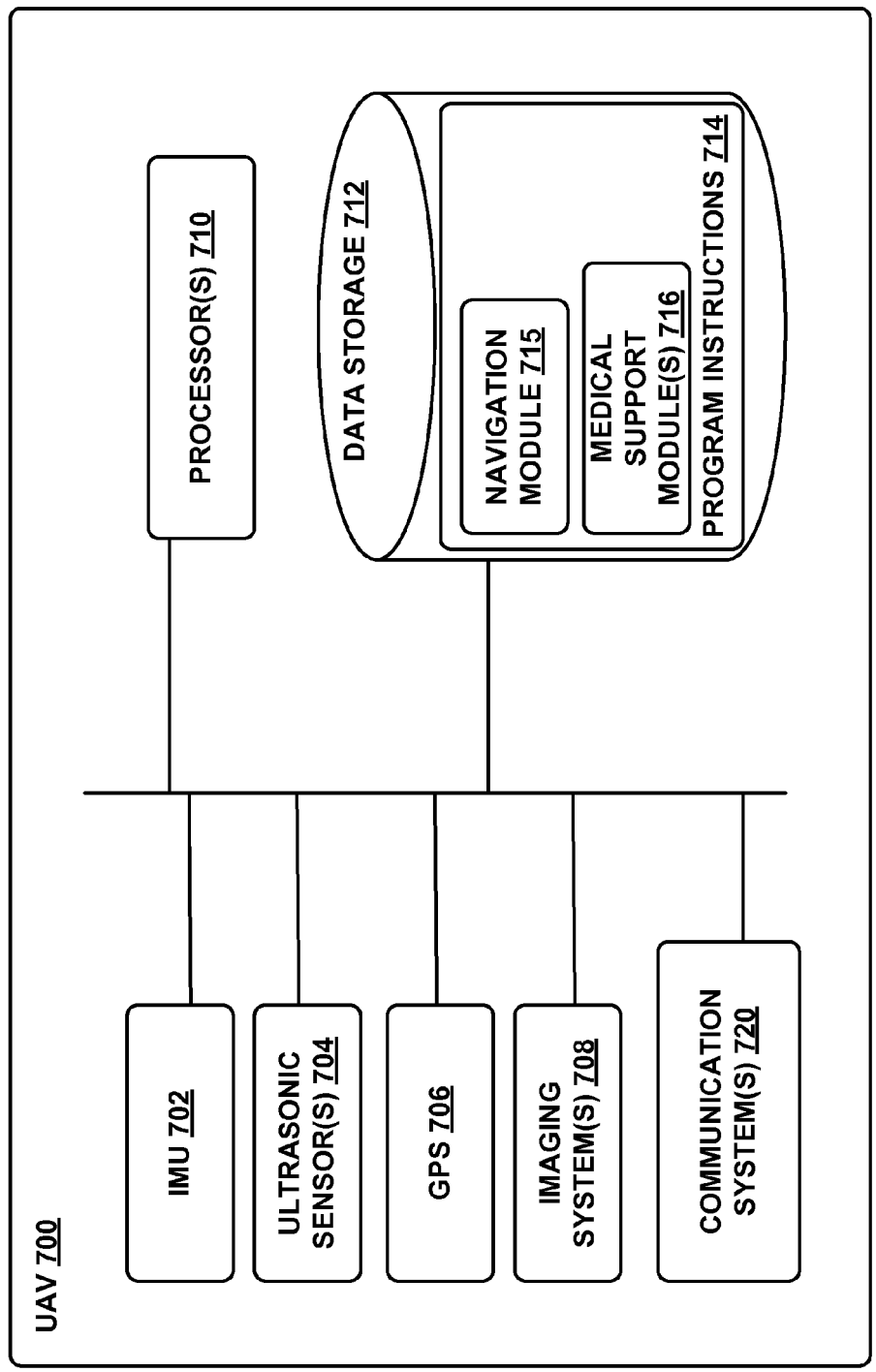
FIG. 7 is a simplified block diagram illustrating components of an unmanned aerial vehicle, according to an example embodiment.

FIG. 7 is a simplified block diagram illustrating components of a UAV 600, according to an example embodiment. UAV 700 may take the form of or be similar in form to one of the UAVs 100, 200, 300, and 350 shown in FIGS. 1, 2, 3A, and 3B. However, a UAV 700 may also take other forms.

UAV 700 may include various types of sensors, and may include a computing system configured to provide the functionality described herein. In the illustrated embodiment, the sensors of UAV 700 include an inertial measurement unit (IMU) 702, ultrasonic sensor(s) 704, GPS 606, imaging system(s) 708, among other possible sensors and sensing systems.

In the illustrated embodiment, UAV 700 also includes one or more processors 710. A processor 710 may be a general-purpose processor or a special purpose processor (e.g., digital signal processors, application specific integrated circuits, etc.). The one or more processors 710 can be configured to execute computer-readable program instructions 714 that are stored in the data storage 712 and are executable to provide the functionality of a UAV described herein.

The data storage 712 may include or take the form of one or more computer-readable storage media that can be read or accessed by at least one processor 710. The one or more computer-readable storage media can include volatile and/or non-volatile storage components, such as optical, magnetic, organic or other memory or disc storage, which can be integrated in whole or in part with at least one of the one or more processors 710. In some embodiments, the data storage 712 can be implemented using a single physical device (e.g., one optical, magnetic, organic or other memory or disc storage unit), while in other embodiments, the data storage 712 can be implemented using two or more physical devices.

As noted, the data storage 712 can include computer-readable program instructions 714 and perhaps additional data, such as diagnostic data of the UAV 700. As such, the data storage 714 may include program instructions to perform or facilitate some or all of the UAV functionality described herein. For instance, in the illustrated embodiment, program instructions 714 include a navigation module 715 and one or more medical-support modules 716.

A. Sensors

In an illustrative embodiment, IMU 702 may include both an accelerometer and a gyroscope, which may be used together to determine the orientation of the UAV 700. In particular, the accelerometer can measure the orientation of the vehicle with respect to earth, while the gyroscope measures the rate of rotation around an axis. IMUs are commercially available in low-cost, low-power packages. For instance, an IMU 702 may take the form of or include a miniaturized MicroElectroMechanical System (MEMS) or a NanoElectroMechanical System (NEMS). Other types of IMUs may also be utilized.

An IMU 702 may include other sensors, in addition to accelerometers and gyroscopes, which may help to better determine position and/or help to increase autonomy of the UAV 700. Two examples of such sensors are magnetometers and pressure sensors. Other examples are also possible. (Note that a UAV could also include such additional sensors as separate components from an IMU.)

While an accelerometer and gyroscope may be effective at determining the orientation of the UAV 700, slight errors in measurement may compound over time and result in a more significant error. However, an example UAV 700 may be able mitigate or reduce such errors by using a magnetometer to measure direction. One example of a magnetometer is a low-power, digital 3-axis magnetometer, which can be used to realize an orientation independent electronic compass for accurate heading information. However, other types of magnetometers may be utilized as well.

UAV 700 may also include a pressure sensor or barometer, which can be used to determine the altitude of the UAV 700. Alternatively, other sensors, such as sonic altimeters or radar altimeters, can be used to provide an indication of altitude, which may help to improve the accuracy of and/or prevent drift of an IMU.

In a further aspect, UAV 700 may include one or more sensors that allow the UAV to sense objects in the environment. For instance, in the illustrated embodiment, UAV 700 includes ultrasonic sensor(s) 704. Ultrasonic sensor(s) 704 can determine the distance to an object by generating sound waves and determining the time interval between transmission of the wave and receiving the corresponding echo off an object. A typical application of an ultrasonic sensor for unmanned vehicles or IMUs is low-level altitude control and obstacle avoidance. An ultrasonic sensor can also be used for vehicles that need to hover at a certain height or need to be capable of detecting obstacles. Other systems can be used to determine, sense the presence of, and/or determine the distance to nearby objects, such as a light detection and ranging (LIDAR) system, laser detection and ranging (LADAR) system, and/or an infrared or forward-looking infrared (FLIR) system, among other possibilities.

UAV 700 also includes a GPS receiver 706. The GPS receiver 706 may be configured to provide data that is typical of well-known GPS systems, such as the GPS coordinates of the UAV 700. Such GPS data may be utilized by the UAV 700 for various functions. For example, when a caller uses a mobile device to request medical support from a UAV, the mobile device may provide its GPS coordinates. As such, the UAV may use its GPS receiver 706 to help navigate to the caller's location, as indicated, at least in part, by the GPS coordinates provided by their mobile device. Other examples are also possible.

UAV 700 may also include one or more imaging system(s) 708. For example, one or more still and/or video cameras may be utilized by a UAV 700 to capture image data from the UAV's environment. As a specific example, charge-coupled device (CCD) cameras or complementary metal-oxide-semiconductor (CMOS) cameras can be used with unmanned vehicles. Such imaging sensor(s) 708 have numerous possible applications, such as obstacle avoidance, localization techniques, ground tracking for more accurate navigation (e.g., by applying optical flow techniques to images), video feedback, and/or image recognition and processing, among other possibilities.

In a further aspect, UAV 700 may use its one or more imaging system 708 to help in determining location. For example, UAV 700 may capture imagery of its environment and compare it to what it expects to see in its environment given current estimated position (e.g., its current GPS coordinates), and refine its estimate of its position based on this comparison.

In a further aspect, UAV 700 may include one or more microphones. Such microphones may be configured to capture sound from the UAVs environment.

B. Navigation and Location Determination

The navigation module 715 may provide functionality that allows the UAV 700 to, e.g., move about in its environment and reach a desired location. To do so, the navigation module 715 may control the altitude and/or direction of flight by controlling the mechanical features of the UAV that affect flight (e.g., rotors 110 of UAV 100).

In order to navigate the UAV 700 to a target location, a navigation module 715 may implement various navigation techniques, such as map-based navigation and localization-based navigation, for instance. With map-based navigation, the UAV 700 may be provided with a map of its environment, which may then be used to navigate to a particular location on the map. With localization-based navigation, the UAV 700 may be capable of navigating in an unknown environment using localization. Localization-based navigation may involve a UAV 700 building its own map of its environment and calculating its position within the map and/or the position of objects in the environment. For example, as a UAV 700 moves throughout its environment, the UAV 700 may continuously use localization to update its map of the environment. This continuous mapping process may be referred to as simultaneous localization and mapping (SLAM). Other navigation techniques may also be utilized.

In some embodiments, the navigation module 715 may navigate using a technique that relies on waypoints. In particular, waypoints are sets of coordinates that identify points in physical space. For instance, an air-navigation waypoint may be defined by a certain latitude, longitude, and altitude. Accordingly, navigation module 715 may cause UAV 700 to move from waypoint to waypoint, in order to ultimately travel to a final destination (e.g., a final waypoint in a sequence of waypoints).

The UAV 700 may include a module or device that is able to signal to a passer-by for assistance in either reaching the specific location or delivering its medical-support items to the medical situation; for example, by displaying a visual message in a graphic display, playing an audio message or tone through speakers, flashing a light, or performing a combination of such functions. Such visual or audio message might indicate that assistance is needed in delivering the UAV 700 to the person in need, and might provide information to assist the passer-by in delivering the UAV 700 to the person, such a description of the person, the person's name, and/or a description of the person's specific location, among other possibilities. This implementation can be useful in a scenario in which the UAV is unable to use sensory functions or another location-determination technique to determine the specific location of the person.

C. Communication Systems

In a further aspect, UAV 700 includes one or more communication systems 720. The communications systems 720 may include one or more wireless interfaces and/or one or more wireline interfaces, which allow UAV 700 to communicate via one or more networks. Such wireless interfaces may provide for communication under one or more wireless communication protocols, such as Bluetooth, WiFi (e.g., an IEEE 802.11 protocol), Long-Term Evolution (LTE), WiMAX (e.g., an IEEE 802.16 standard), a radio-frequency ID (RFID) protocol, near-field communication (NFC), and/or other wireless communication protocols. Such wireline interfaces may include an Ethernet interface, a Universal Serial Bus (USB) interface, or similar interface to communicate via a wire, a twisted pair of wires, a coaxial cable, an optical link, a fiber-optic link, or other physical connection to a wireline network.

In an example embodiment, a UAV 700 may include communication systems 720 that allow for both short-range communication and long-range communication. For example, the UAV 700 may be configured for short-range communications using Bluetooth and for long-range communications under a CDMA protocol. In such an embodiment, the UAV 700 may be configured to function as a "hot spot;" or in other words, as a gateway or proxy between a remote support device and one or more data networks, such as cellular network and/or the Internet. Configured as such, the UAV 700 may facilitate data communications that the remote support device would otherwise be unable to perform by itself.

For example, UAV 700 may provide a WiFi connection to a remote device, and serve as a proxy or gateway to a cellular service provider's data network, which the UAV might connect to under an LTE or a 3G protocol, for instance. The UAV 700 could also serve as a proxy or gateway to a high-altitude balloon network, a satellite network, or a combination of these networks, among others, which a remote device might not be able to otherwise access.

D. Power Systems

In a further aspect, UAV 700 may include power system(s) 721. A power system 721 may include one or more batteries for providing power to the UAV 700. In one example, the one or more batteries may be rechargeable and each battery may be recharged via a wired connection between the battery and a power supply and/or via a wireless charging system, such as an inductive charging system that applies an external time-varying magnetic field to an internal battery.

E. Medical-Support Functionality

As noted above, UAV 700 may include one or more medical-support modules 716. The one or more medical-support modules 716 include software, firmware, and/or hardware that may help to provide or assist in the provision of the medical-support functionality described herein.

A UAV 700 may have stored information on an associated alert device, such as ADs 607, that can be provided to a person or persons within or nearby the target location, in order to assist the person or persons in transporting the UAV 700 or contents of the UAV 700 to the scene of a situation to provide medical or other emergency relief care. Part of assisting the person or persons in transporting the UAV 700 or contents of the UAV 700 may include the alert device issuing instructions, as discussed above. Additionally, the alert device may comprise a video or audio file with directions regarding where to take the UAV or the associated medical supplies. The alert device may comprise a video or an audio file with either instructions for transportation of the UAV 700, instructions for providing support, or both. As another example, an alert device may include an interactive program to assist a person in providing medical support. For instance, an alert device may include an application that analyzes the person's speech to detect questions related to the medical situation and/or that provides a text-based user interface via which the person can ask such questions, and then determines and provides answers to such questions.

In some embodiments, an alert device associated with UAV 700 may facilitate communication between a layperson and/or medical personnel at the scene and medical personnel at a remote location. As an example, a medical support module 716 may provide a user interface via which a person at the scene can use a communication system 720 of the UAV to communicate with an emergency medical technician at a remote location, such as described with reference to FIG. 6.

Items that may aid in diagnosing and/or treating a person who needs medical assistance, or may serve other purposes may include, as examples: (a) medicines, (b) diagnostic devices, such as a pulse oximeter, blood pressure sensor, or EKG sensor, (c) treatment devices, such as an EpiPen, a first aid kit, or various kinds of defibrillators (e.g., an automated external defibrillator (AED)), (d) food, (e) other disaster relief supplies, such as clothing, for example, and/or (f) remote support devices, such as a mobile phone or a head-mountable device (HMD), among other possibilities. Note that some items that are electronic may include one or more batteries to provide power to the item. In addition or on in the alternative, an item may be integrated with one or more batteries in the power system 621 for power.

A UAV 700 may employ various systems and configurations in order to transport items to the target location, for further transportation to the scene of a situation. For example, as shown in FIG. 1, a UAV 100 can include a compartment 135, in which an item or items may be transported. As another example, the UAV can include a pick-and-place mechanism, which can pick up and hold the item while the UAV is in flight, and then release the item during or after the UAV's descent. As yet another example, a UAV could include an air-bag drop system, a parachute drop system, and/or a winch system that is operable from high above a medical situation to drop or lower an item or items to the scene of the medical situation. In these previous two embodiments, an alert device may be present on the item that is released. Other examples are also possible.

In some implementations, a given UAV 700 may include a "package" designed for a particular medical situation (or possibly for a particular set of medical situations). A package may include one or more items for medical support in the particular medical situation, and/or one or more medical-support modules 716 that are designed to provide medical support in the particular medical situation. In some cases, a UAV 700 may include a package that is designed for a particular medical situation such as choking, cardiac arrest, shock, asthma, drowning, etc.

A UAV may have an integrated medical-support device. For example, a UAV 700 might function as a mobile defibrillator. Thus, rather than carry a stand-alone defibrillator that can then be removed from the UAV for use, the UAV itself may function as a defibrillator.

Many other examples and variations on the above examples of UAVs with integrated medical-support systems and devices are also possible. For instance, a medical device may be integrated into the structure of a UAV itself when doing so reduces weight, improves aerodynamics, and/or simplifies the use of the device by a person at the scene of the medical situation. Further, those skilled in the art will appreciate that a medical-support system or device may be integrated in the structure of a UAV in other situations and for other reasons.

It should be understood that the examples of medical-support functionality that are provided herein are not intended to be limited. A UAV may be configured to provide other types of medical-support functionality without departing from the scope of the invention.

V. Illustrative Methods

Figure 8:
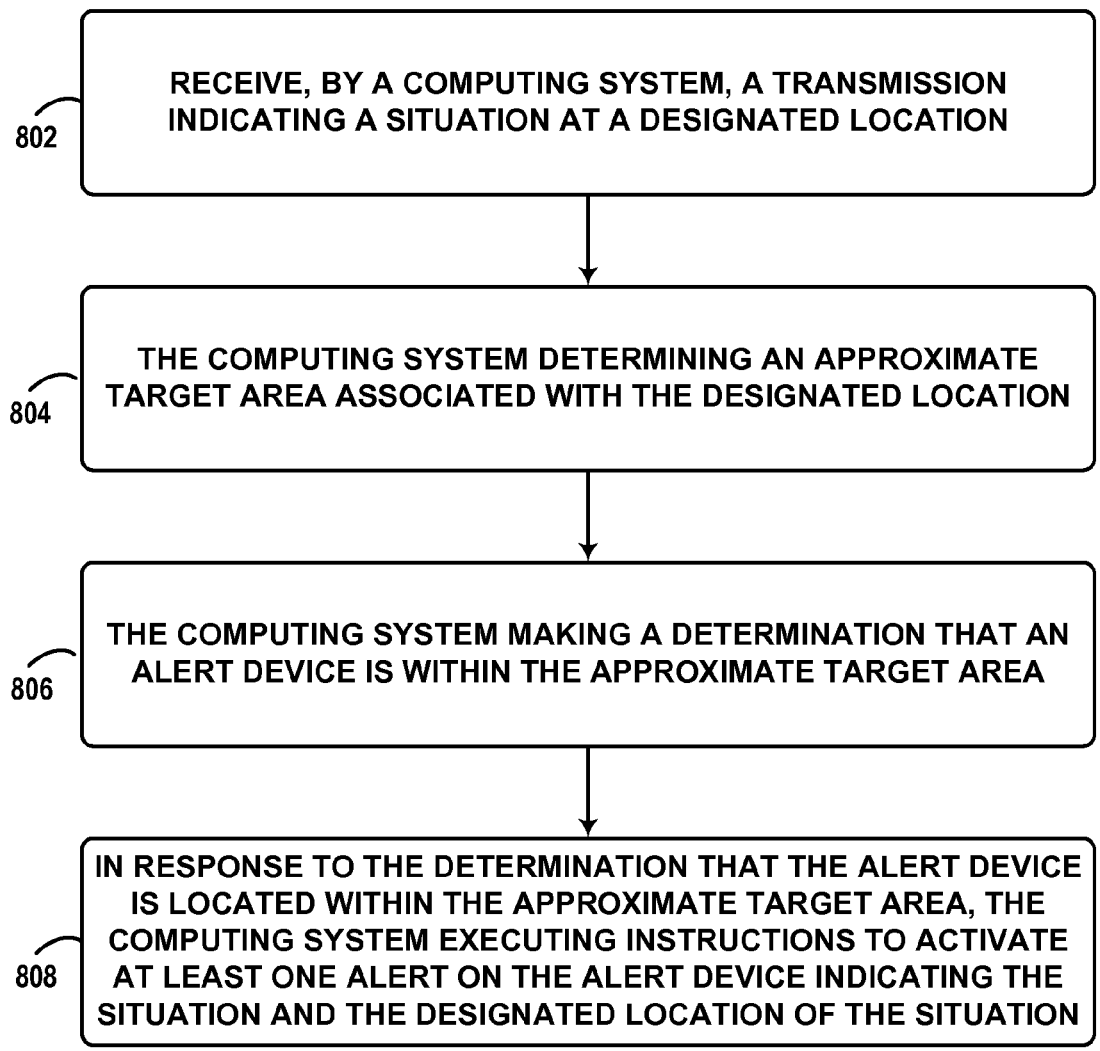
FIG. 8 is a flow chart illustrating a method, according to an example embodiment.

FIG. 8 is a flow chart illustrating a method 800 according to an example embodiment. Method 800 may be implemented by a device in order to alert and instruct one or more individuals near the device to obtain and/or use an item in a support situation.

Illustrative methods, such as method 800, may be implemented by fixed-location hardware, such as the fixed-location hardware described in reference to FIG. 4, by a UAV, such as the UAVs described in reference to FIGS. 1 to 3, or by one or more components of such fixed-location hardware or UAVs. In other embodiments, some or all of an example method may be carried out by a remote computing device that is in communication with such a device. For example, some or all of an exemplary method may be carried out by a support system, such as by the one or more of the components of the support systems 400 or 600 shown in FIGS. 4 and 6.

Referring to FIG. 8, method 800 involves receiving, by a computing system, a transmission indicating a situation at a designated location, as shown by block 802. The transmission may be received from a number of entities, such as those discussed above with respect to FIGS. 4-6. The situation may comprise a medical, emergency, disaster, or other type of situation discussed herein.

The method 800 then involves the computing system determining an approximate target area associated with the designated location, as shown by block 804. Various techniques may be used to determine the approximate target area. Further, the approximate target area may take various forms. For example, the approximate target area could be provided in the form of GPS coordinates, at a certain latitude and longitude, a street address, and/or a certain place (e.g., a particular building, stadium, landmark, or park), among other possibilities.

In some embodiments, the approximate target area may comprise a circle with a specified radius, wherein the circle is determined to surround the precise scene of a situation.

In other embodiments, the approximate target area may be an estimated location of the person or persons who are likely to benefit from medical support in the given medical situation. For example, if a person who is need of medical care places an emergency call from their own mobile phone, the approximate target location may be determined to be or otherwise based on the location of their mobile phone.

In other embodiments, the approximate target area may be different from the location of the person or persons who are likely to benefit from medical support. For example, consider a scenario where an emergency medical technician (EMT) or paramedic is closer to the location of a person in need of medical support, but the EMT or paramedic does not have certain medical supplies that are needed for or might improve the medical care that can be provided. In this scenario, a medical support system may dispatch a UAV to the location of the EMT or paramedic in order to deliver medical supplies to the EMT or paramedic, so that they can take them with them to the scene of the medical situation. Further, in some cases, the UAV might even be configured to deliver the medical supplies to the EMT or paramedic as they travel to the scene of the medical situation. In such case, the approximate target location (e.g., the location of the EMT or paramedic) may be dynamically updated to reflect the movement of the EMT or paramedic as they travel to the scene.

Further, the method 800 involves the computing system making a determination that an alert device is located within the approximate target area, as shown by block 806. In response, the computing system executes instructions to activate at least one alert on the alert device indicating the emergency situation and the designated location of the emergency situation, as shown by block 808.

Note that in an example embodiment, method 800 may be carried out entirely by a UAV. As such, the determination of the target location at block 802 may simply involve the UAV receiving a data message that indicates the target location, such as a message indicating the GPS coordinates of a remote device from which medical support was requested, for instance. As such, the logic to actively determine what the target location is for a given medical situation may be implemented at a component or component of a medical support system, such as an access system and/or a dispatch system.

In another example embodiment, method 800 may be carried out by a system such as system 400, which involves a computing system controlling an alert device associated with fixed-location hardware.

A support system may determine and/or be provided with information that then can be used to determine the target location, or scene of a situation, in other ways. For instance, in some embodiments, part or all of the process of determining the target location could be automated or, in other words, performed without a need for human intervention. To this end, the medical support system could utilize any suitable information-recognition technique, such as, for example, voice recognition (when the notification is spoken) or character recognition (when the notification is typed), among other techniques now known or later developed. As an example, consider a scenario where a bystander calls "911" and says: "Somebody near me just collapsed! I'm at 123 Main Street, Mountain View." In this situation, an automated dispatch system could apply speech-to-text processing to analyze the bystander's words and determine the stated address therefrom.

Other types of location information may also be utilized to determine the target location. For example, the medical support system may obtain location information from image data that is captured by a remote device at the scene of a medical situation, and sent from the remote device to a medical support system. For example, a notifier may use the camera of their mobile phone to capture and send video and/or still images to the medical support system, possibly in real-time. A component of a medical support system could then analyze such image data to detect, e.g., street signs and/or landmarks such as buildings or sculptures, which may help to identify the location of a medical situation.

The above techniques for determining the approximate target location associated with a medical situation are provided for illustrative purposes and not intended to be limiting.

It should be understood that other techniques may be used to determine the approximate target location, without departing from the scope of the invention.

At block 806, a system may use various techniques to determine that an alert device is located at the approximate target location. For example, if the alert device is present on a UAV and if the approximate target location is the GPS coordinates of the remote device from which the medical situation was reported, then a UAV may use its GPS system to determine when it has reached those GPS coordinates. Alternatively, the UAV may consider itself to have reached the approximate target location when it is within a certain distance from the GPS coordinates (e.g., within 100 feet).

As another example, if the approximate target location is a particular landmark (e.g., a particular building, a stadium, a park, or a certain beach), then a UAV may utilize its GPS system and/or another location-determination system in conjunction with mapping data to determine when the UAV is located at or near a location that the mapping data associates with the particular landmark. Such mapping data may be included in the data storage of a UAV, or may be provided to a UAV by a remote mapping server.

iv. Illustrative Application

FIG. 9 is an illustration of a scenario 900 in which example methods, such as method 800, could be implemented. As shown in scenario 900, a UAV 902 may be located at a deployment system 904, which may be on top of a firehouse 906. Further, UAV 902 may include an alert device 907. The alert device 907 includes both an audio alert and a visual alert, each of which may be activated by a remote user.

In scenario 900, a medical support system may receive a request from a user of a mobile phone 908 to provide medical support at a medical situation occurring in a house 910. When the request is received, the medical support system may obtain GPS coordinates indicating a location 912 of the house 910. Note that in scenario 900, within the house 910 is located at the scene of the medical situation. However, due to obstacles, such as the roof, walls, closed windows, and door of the house 910, the UAV 902 and/or the alert device 907 would have difficulty entering the house.

When the medical support system receives the request for medical support, the medical support system may provide the GPS coordinates received for the house 910 to the UAV 902. Accordingly, UAV 902 may set an area around location 912 to be an approximate target area 913 and use a navigation process to navigate to a location within the approximate target area 913.

When UAV 902 arrives at the approximate target area 913, UAV 902 may either land, containing the medical supplies for the medical situation and the alert device 907, or may release a package, such as that described with reference to FIG. 7, containing appropriate medical supplies for the medical situation, wherein the alert device 907 is present on the released package. Thus, the actual location of the medical supplies is some distance from the medical situation (e.g., 50 feet away).

A remote operator, upon the occurrence of a trigger (e.g., landing of the UAV 802 on the ground), activates the alert device 907, which then proceeds to issue both a visual alert 909 and an audio alert 911. A bystander outside of the house 910 may then notice the package, go to the package, and either read instructions on a user interface on the alert device 907 or listen to audio instructions issued from a speaker on the alert device 907 regarding what to do with the package. For example, the instructions may indicate that the bystander should take the package inside the house 910, whereby the bystander will go up to a door on the house 910, ring the doorbell or knock on the door to attract the attention of individuals within the house 910.

In this manner, alert device 907 is an effective way to get critical packages to a scene of a situation in an efficient manner. The alert device 907 is able to crowdsource bystanders in the vicinity of a critical package, without those bystanders having to subscribe or otherwise belong to an alert service or system. Thus, the alert device 907 and methods described herein, such as method 800, are able to get a critical package or hardware from a location near a scene of a situation to the actual scene of the situation, quickly helping those in need.

Further, it should be understood that the above is but one of many possible applications of an example method. Other applications are also possible.

VI. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

The invention claimed is:

1. An unmanned aerial vehicle (UAV) comprising:
a navigation module that provides a navigation process to generate flight-control signals for the UAV;
one or more emergency supplies positioned on the UAV;
an alert device associated with the one or more emergency supplies, wherein the alert device, when activated, emits at least one of an audio and a visual signal to draw attention to the emergency supplies; and
a control system configured to cause the UAV to:
receive a transmission indicating an emergency situation at a designated location;
determine an approximate target area associated with the designated location;
in response to the determination that the one or more emergency supplies are applicable to the emergency situation, navigate from a launch site to the approximate target area associated with the designated location;
in response to a determination that the UAV is located within the approximate target area, deliver the one or more emergency supplies to a ground level location within the approximate target area; and
in response to a determination that the one or more emergency supplies are positioned at the ground level location, activate at least one alert on the alert device indicating the emergency situation and the designated location of the emergency situation.

2. The UAV of claim 1, wherein the alert device displays instructions on a user interface to deliver the emergency supplies to the emergency situation.

3. The UAV of claim 1, wherein the alert device displays instructions on a user interface regarding how to handle the emergency supplies associated with the alert device.

4. The UAV of claim 1, wherein a scene of an emergency situation is known but is not immediately accessible by the UAV.

5. The UAV of claim 1, wherein the at least one alert on the alert device includes a description of the type of emergency situation.

6. A method comprising:
receiving, by a computing system, a transmission indicating an emergency situation at a designated location;
the computing system determining an approximate target area associated with the designated location;
the computing system making a determination that emergency fixed-location hardware is located within the approximate target area, wherein the emergency fixed-location hardware is maintained in a stationary position at a particular location when not in use, and wherein an alert device is positioned on the emergency fixed-location hardware;
the computing system making a determination that the emergency fixed-location hardware is applicable to the emergency situation; and
in response to the determination that the emergency fixed-location hardware is applicable to the emergency situation and located within the approximate target area, the computing system activating at least one alert on the alert device indicating the emergency situation and the designated location of the emergency situation.

7. The method of claim 6, wherein the instructions to activate at least one alert on the alert device comprises instructions to activate a visual alert.

8. The method of claim 6, wherein the instructions to activate at least one alert on the alert device comprises instructions to activate an audio alert.

9. The method of claim 6, wherein the instructions to activate at least one alert on the alert device comprises instructions to activate both a visual alert and an audio alert.

10. The method of claim 6, wherein the at least one alert on the alert device includes visually displayed instructions regarding how to handle the emergency fixed-location hardware.

* * * * *